United States Patent
Andersson et al.

(10) Patent No.: US 10,469,963 B2
(45) Date of Patent: Nov. 5, 2019

(54) SUSPENDED COMPONENTS IN AUDITORY PROSTHESES

(71) Applicant: COCHLEAR LIMITED, Macquarie University (AU)

(72) Inventors: Marcus Andersson, Mölnlycke (SE); Johan Gustafsson, Mölnlycke (SE); Dan Nyström, Mölnlycke (SE); Henrik Fyrlund, Mölnlycke (SE)

(73) Assignee: COCHLEAR LIMITED, Macquarie University (AU)

( * ) Notice: Subject to any disclaimer, the term of this patent is extended or adjusted under 35 U.S.C. 154(b) by 261 days.

(21) Appl. No.: 14/832,973

(22) Filed: Aug. 21, 2015

(65) Prior Publication Data

US 2016/0058555 A1 Mar. 3, 2016

Related U.S. Application Data

(60) Provisional application No. 62/043,013, filed on Aug. 28, 2014.

(51) Int. Cl.
*H04R 25/00* (2006.01)
*A61N 1/36* (2006.01)

(52) U.S. Cl.
CPC ........ *H04R 25/606* (2013.01); *A61N 1/36038* (2017.08); *H04R 2460/13* (2013.01)

(58) Field of Classification Search
CPC ............ H04R 2460/13; H04R 2225/67; H04R 25/60; H04R 25/604; H04R 25/65; H04R 31/006; A61N 1/375
USPC .......................................................... 600/25
See application file for complete search history.

(56) References Cited

U.S. PATENT DOCUMENTS

| | | | | |
|---|---|---|---|---|
| 4,736,747 A | * | 4/1988 | Drake | A61N 1/375 607/61 |
| 2003/0012395 A1 | * | 1/2003 | Fukuda | H04R 13/00 381/380 |
| 2003/0034705 A1 | | 2/2003 | Hakansson | |
| 2006/0045298 A1 | | 3/2006 | Westerkull | |
| 2007/0053536 A1 | * | 3/2007 | Westerkull | H04R 25/606 381/326 |

(Continued)

FOREIGN PATENT DOCUMENTS

KR 10-2008-0003627 A 1/2008

OTHER PUBLICATIONS

PCT International Search Report and Written Opinion in International Application PCT/IB2015/001952, dated Mar. 28, 2016, 12 pgs.

(Continued)

*Primary Examiner* — Kaylee R Wilson
(74) *Attorney, Agent, or Firm* — Merchant & Gould P.C.

(57) ABSTRACT

An external portion of an auditory prosthesis includes magnets, electronics, and other components. In bone conduction auditory prostheses, reducing the amount of mass subject to vibrations in an auditory prosthesis has a positive effect on tuning of the device. One way of reducing such mass is to resiliently more massive components within the auditory prosthesis housing. Such resilient mounting reduces the dampening effect that these massive components have on vibrations generated by the prosthesis. When electronic components are suspended, feedback to said components is also reduced, resulting improved performance.

26 Claims, 10 Drawing Sheets

(56) References Cited

U.S. PATENT DOCUMENTS

| | | |
|---|---|---|
| 2008/0319250 A1 | 12/2008 | Asnes |
| 2009/0245553 A1 | 10/2009 | Parker |
| 2009/0285417 A1* | 11/2009 | Shin .................. H04M 1/03 381/151 |
| 2011/0301404 A1 | 12/2011 | Bern |
| 2012/0083860 A1* | 4/2012 | Hakansson ............ H04R 1/288 607/57 |
| 2012/0237067 A1* | 9/2012 | Asnes .................... H04R 9/025 381/326 |
| 2012/0302822 A1* | 11/2012 | Van Himbeeck .... H04R 25/606 600/25 |
| 2013/0096367 A1* | 4/2013 | Easter .................. A61F 11/045 600/25 |
| 2013/0114834 A1 | 5/2013 | Bern |
| 2013/0195304 A1 | 8/2013 | Andresson |
| 2014/0012071 A1 | 1/2014 | Nagl et al. |
| 2015/0049889 A1 | 2/2015 | Bern |

OTHER PUBLICATIONS

Extended European Search Report in Application No. 15836617.9, dated Mar. 27, 2018, 9 pages.
Chinese Office Action in Application No. 201580046239.5 dated Aug. 3, 2018, 12 pages.

* cited by examiner

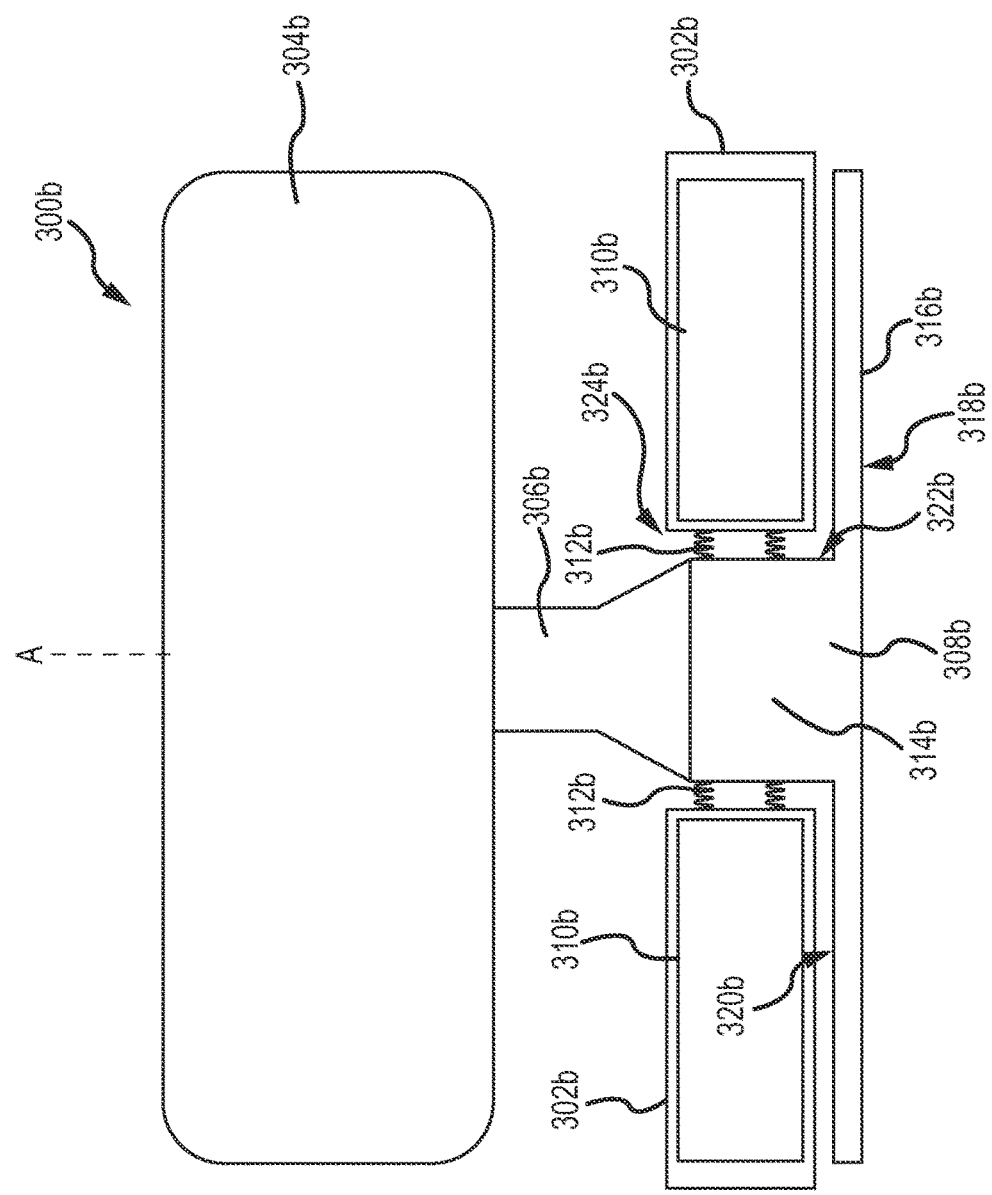

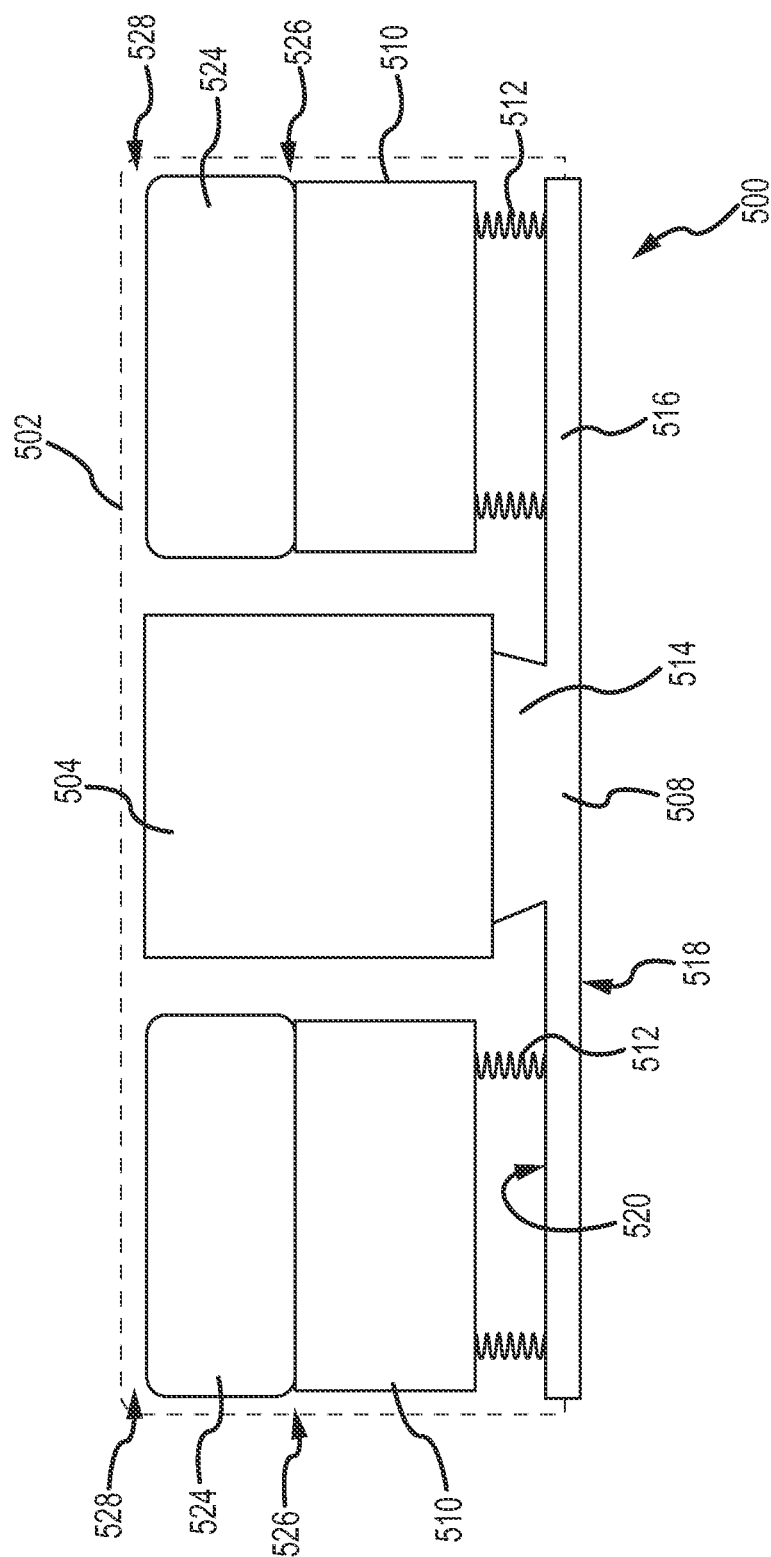

SUSPENDED COMPONENTS IN AUDITORY PROSTHESES

BACKGROUND

An auditory prosthesis can be placed on the skull of a recipient to deliver a stimulus in the form of a vibration to the skull. These types of auditory prosthesis are generally referred to as bone conduction devices. The auditory prosthesis receives sound via a microphone located on a head-mounted processor. The head-mounted processor is secured to the head with a magnet that interacts with a magnet implanted in the head of the recipient. Processed sound signals are delivered as a vibration stimulus from the external portion to a bone anchor via the implanted magnet. The bone anchor vibrates the skull of the recipient at the appropriate frequency to generate a hearing percept. The magnets form a mass that can make tuning of the auditory prosthesis difficult, due to the dampening of vibrations by the mass.

SUMMARY

Reducing the amount of mass subject to vibrations in an auditory prosthesis has a positive effect on tuning of the device. One way of reducing such mass is to resiliently mount magnets, electronics, and other components within the auditory prosthesis housing. Such resilient mounting reduces the dampening effect that these massive components have on vibrations generated by the prosthesis. When electronic components are suspended, feedback to said components is also reduced, resulting improved performance.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

FIGS. 3A-3C depict partial cross-sectional schematic views of external portions of transcutaneous bone conduction devices.

FIG. 5 depicts a partial cross-sectional schematic view of an external portion of a transcutaneous bone conduction device.

DETAILED DESCRIPTION

The technologies described herein can typically be utilized with transcutaneous bone conduction devices. Such devices utilize one or more magnets disposed in an external portion and/or implanted portion of the bone conduction device. The magnetic field of an external magnet interacts with a magnetic field of a magnet disposed in an implanted portion of the bone conduction device. The technologies described herein are also applicable to percutaneous bone conduction prostheses that utilize an anchor that penetrates the skin of the head. An external portion of the auditory prosthesis is secured to the anchor with, e.g., a snap connection. By utilizing the technologies described herein, the anchor can be manufactured in whole or in part of a magnetic material, and a mating magnetic material can be disposed in the external portion to mate with the anchor, either alone, or also in conjunction with a snap connection. Additionally, the technologies described herein contemplate a single bone conduction device that can be utilized in both percutaneous and transcutaneous applications. Such devices can include a housing containing sound processing components, microphones, and a vibration element. When used in a percutaneous application, the vibration element can be directly connected to the anchor that penetrates the skin. When used in a transcutaneous application, a module can be attached to the vibration element and then held on the skin via, e.g., the magnetic components described above.

Figure 1A:
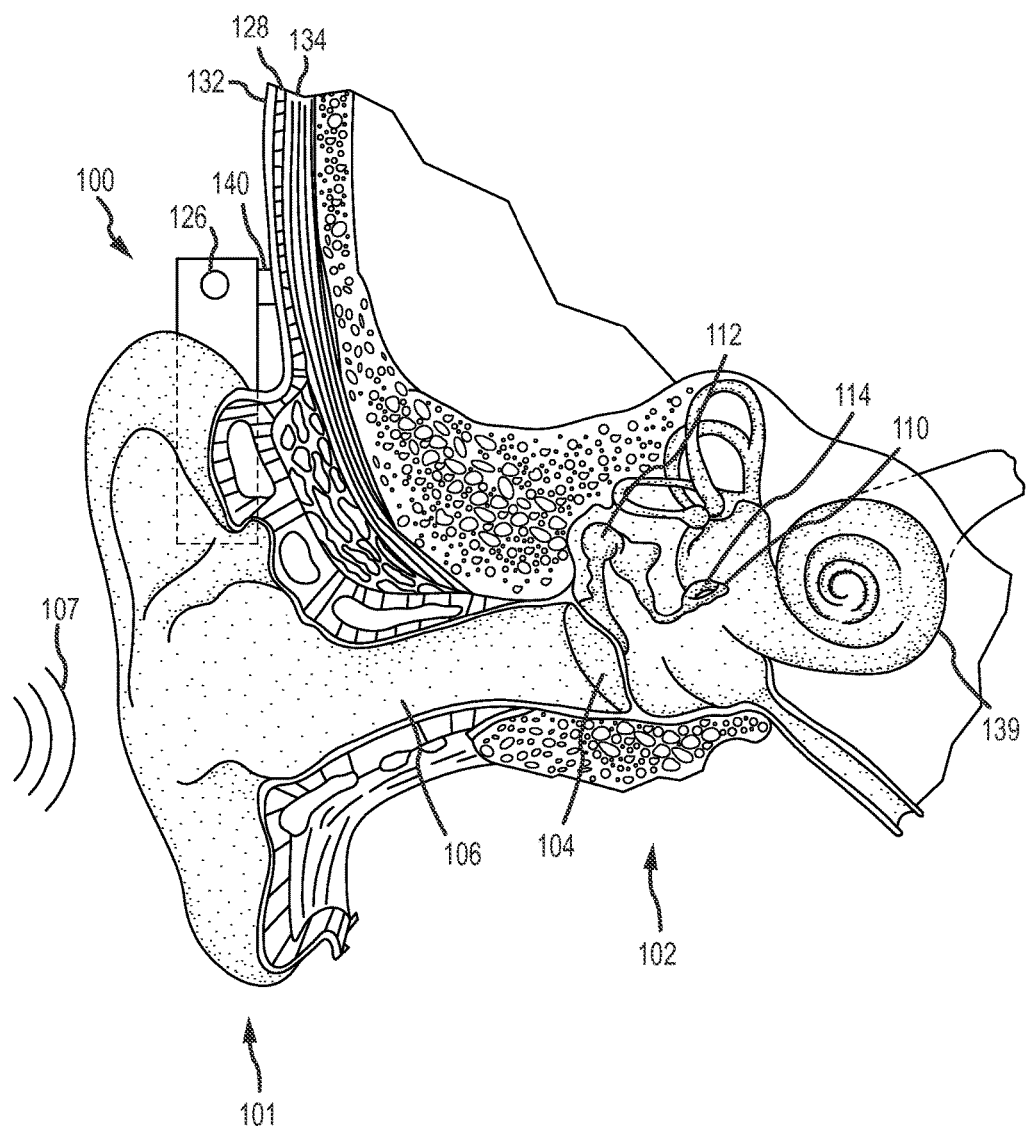
FIG. 1A depicts a partial perspective view of a percutaneous bone conduction device worn on a recipient.

FIG. 1A depicts a partial perspective view of a percutaneous bone conduction device 100 positioned behind outer ear 101 of the recipient and comprises a sound input element 126 to receive sound signals 107. The sound input element 126 can be a microphone, telecoil or similar. In the present example, sound input element 126 can be located, for example, on or in bone conduction device 100, or on a cable extending from bone conduction device 100. Also, bone conduction device 100 comprises a digital sound processor (not shown), a vibrating electromagnetic actuator and/or various other operational components.

More particularly, sound input device 126 converts received sound signals into electrical signals. These electrical signals are processed by the sound processor. The sound processor generates control signals that cause the actuator to vibrate. In other words, the actuator converts the electrical signals into mechanical force to impart vibrations to skull bone 136 of the recipient.

Bone conduction device 100 further includes coupling apparatus 140 to attach bone conduction device 100 to the recipient. In the example of FIG. 1A, coupling apparatus 140 is attached to an anchor system (not shown) implanted in the recipient. An exemplary anchor system (also referred to as a fixation system) can include a percutaneous abutment fixed to the recipient's skull bone 136. The abutment extends from skull bone 136 through muscle 134, fat 128 and skin 132 so that coupling apparatus 140 can be attached thereto. Such a percutaneous abutment provides an attachment location for coupling apparatus 140 that facilitates efficient transmission of mechanical force.

It is noted that sound input element 126 can comprise devices other than a microphone, such as, for example, a telecoil, etc. In an exemplary embodiment, sound input element 126 can be located remote from the BTE device 100 and can take the form of a microphone or the like located on a cable or can take the form of a tube extending from the BTE device 100, etc. Alternatively, sound input element 126 can be subcutaneously implanted in the recipient, or positioned in the recipient's ear canal or positioned within the pinna. Sound input element 126 can also be a component that receives an electronic signal indicative of sound, such as, from an external audio device. For example, sound input element 126 can receive a sound signal in the form of an electrical signal from an MP3 player or a smartphone electronically connected to sound input element 126.

The sound processing unit of the BTE device 100 processes the output of the sound input element 126, which is typically in the form of an electrical signal. The processing unit generates control signals that cause an associated actuator to vibrate. In other words, the actuator converts the electrical signals into mechanical vibrations for delivery to the recipient's skull. These mechanical vibrations are delivered by an external portion of the auditory prosthesis 100, as described below.

Figure 1B:
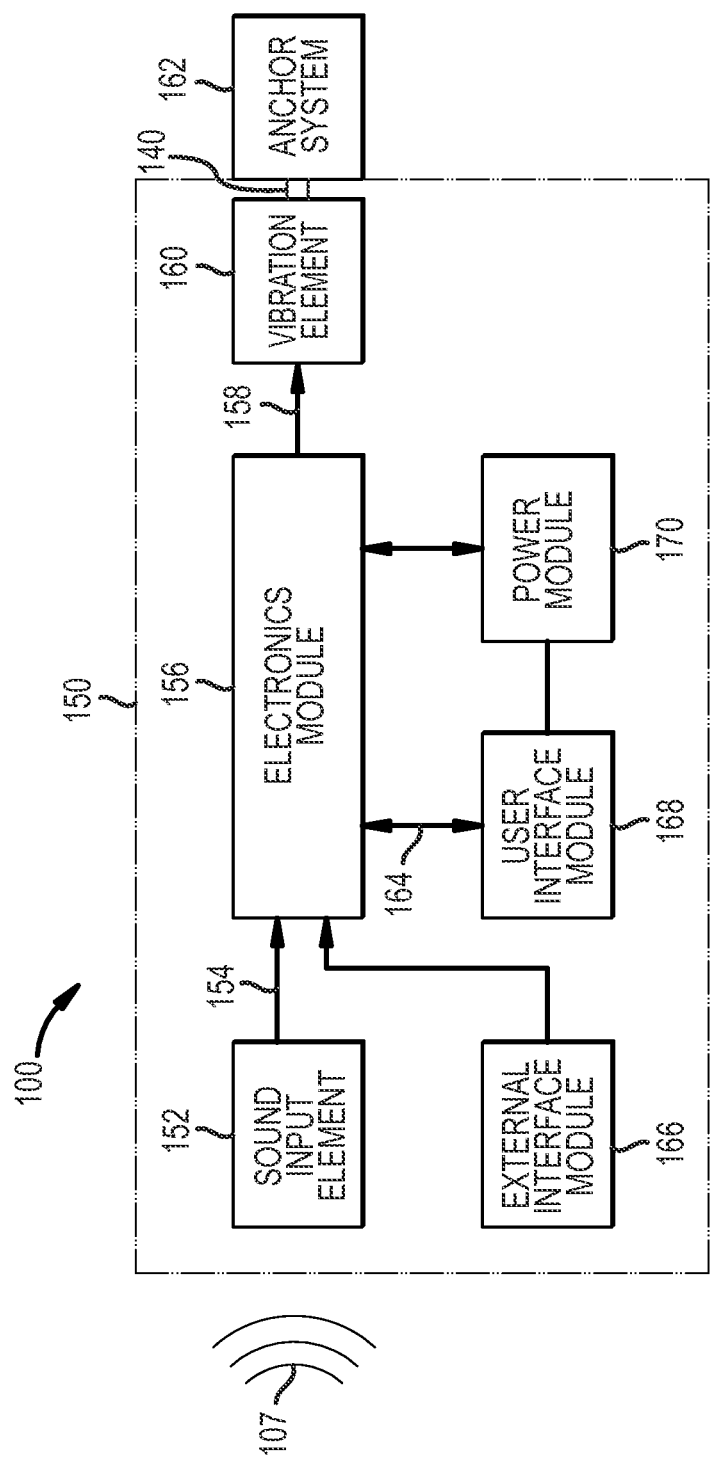
FIG. 1B is a schematic diagram of a percutaneous bone conduction device.

FIG. 1B is a schematic diagram of a percutaneous bone conduction device 100. Sound 107 is received by sound input element 152. In some arrangements, sound input element 152 is a microphone configured to receive sound 107, and to convert sound 107 into electrical signal 154. Alternatively, sound 107 is received by sound input element 152 as an electrical signal. As shown in FIG. 1B, electrical signal 154 is output by sound input element 152 to electronics module 156. Electronics module 156 is configured to convert electrical signal 154 into adjusted electrical signal 158. As described below in more detail, electronics module 156 can include a sound processor, control electronics, transducer drive components, and a variety of other elements.

As shown in FIG. 1B, transducer or vibration element 160 receives adjusted electrical signal 158 and generates a mechanical output force in the form of vibrations that is delivered to the skull of the recipient via a coupling apparatus 140, as described above. The coupling apparatus 140 connects to the anchor system 162, so as to couple the anchor system 162 to bone conduction device 100. Delivery of this output force causes motion or vibration of the recipient's skull, thereby activating the hair cells in the recipient's cochlea (not shown) via cochlea fluid motion.

FIG. 1B also illustrates power module 170. Power module 170 provides electrical power to one or more components of bone conduction device 100. For ease of illustration, power module 170 has been shown connected only to user interface module 168 and electronics module 156. However, it should be appreciated that power module 170 can be used to supply power to any electrically powered circuits/components of bone conduction device 100.

User interface module 168, which is included in bone conduction device 100, allows the recipient to interact with bone conduction device 100. For example, user interface module 168 can allow the recipient to adjust the volume, alter the speech processing strategies, power on/off the device, etc. In the example of FIG. 1B, user interface module 168 communicates with electronics module 156 via signal line 164.

Bone conduction device 100 can further include external interface module that can be used to connect electronics module 156 to an external device, such as a fitting system. Using external interface module 166, the external device, can obtain information from the bone conduction device 100 (e.g., the current parameters, data, alarms, etc.) and/or modify the parameters of the bone conduction device 100 used in processing received sounds and/or performing other functions.

In the example of FIG. 1B, sound input element 152, electronics module 156, vibration element 160, power module 170, user interface module 168, and external interface module have been shown as integrated in a single housing, referred to as housing 150. However, it should be appreciated that in certain examples, one or more of the illustrated components can be housed in separate or different housings. Similarly, it should also be appreciated that in such embodiments, direct connections between the various modules and devices are not necessary and that the components can communicate, for example, via wireless connections.

Figure 2:
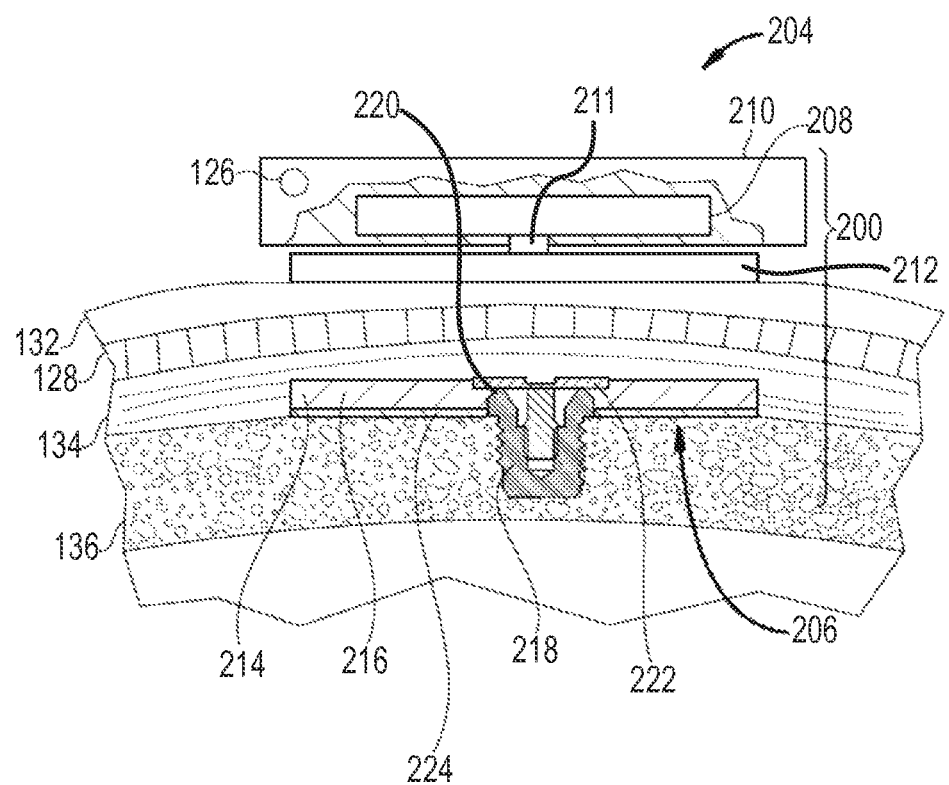
FIG. 2 depicts a cross-sectional schematic view of a transcutaneous bone conduction device worn on a recipient.

FIG. 2 depicts an exemplary embodiment of a transcutaneous bone conduction device 200 that includes an external portion 204 and an implantable portion 206. The transcutaneous bone conduction device 200 of FIG. 2 is a passive transcutaneous bone conduction device in that a transducer or vibration element 208 is located in the external portion 204. In general, the external portion 204 can include the control and sound processing components depicted above in FIG. 1B. For clarity however, these components are generally not depicted; instead, structural elements particular to a transcutaneous bone conduction device 200 are shown. Vibration element 208 is located in housing 210 of the external component, and is coupled via a coupling apparatus 211 to the plate 212, which can be discrete from the housing 210 as depicted, or disposed within the housing 210. Plate 212 can be in the form of a permanent magnet and/or in another form that generates and/or is reactive to a magnetic field, or otherwise permits the establishment of magnetic attraction between the external portion 204 and the implantable portion 206 sufficient to hold the external portion 204 against the skin of the recipient. In other embodiments, magnets or magnetic materials can be discrete from plate 212. Magnetic attraction can be further enhanced by utilization of a magnetic implantable plate 216. In alternative embodiments, multiple magnets in both the external portion 204 and implantable portion 206 can be utilized.

In an exemplary embodiment, the vibration element 208 is a device that delivers vibration stimulus to the skull of a recipient. In operation, sound input element 126 converts sound into electrical signals. Specifically, the transcutaneous bone conduction device 200 provides these electrical signals to vibration element 208, or to a sound processor (not shown) that processes the electrical signals, and then provides those processed signals to vibration element 208. The vibration element 208 converts the electrical signals (processed or unprocessed) into vibrations. Because vibration element 208 is mechanically coupled to plate 212, the vibrations are transferred from the vibration element 208 to plate 212 via coupling apparatus 211. Implantable plate assembly 214 is part of the implantable portion 206, and can be made of a ferromagnetic material that can be in the form of a permanent magnet, that generates and/or is reactive to a magnetic field, or otherwise permits the establishment of a magnetic attraction between the external portion 204 and the implantable portion 206 sufficient to hold the external portion 204 against the skin 132 of the recipient. Accordingly, vibrations produced by the vibration element 208 of the external portion 204 are transferred from plate 212 across the skin 132 to implantable plate 216 of implantable plate assembly 214. This can be accomplished as a result of mechanical conduction of the vibrations through the skin 132, resulting from the external portion 204 being in direct contact with the skin 132 and/or from the magnetic field between the two plates 212, 216. These vibrations are transferred without a component penetrating the skin 132, fat 128, or muscular 134 layers on the head.

As can be seen, the implantable plate assembly 214 is substantially rigidly attached to bone fixture 220 in this embodiment. Implantable plate assembly 214 includes through hole 220 that is contoured to the outer contours of the bone fixture 218, in this case, a bone screw that is secured to the bone 136 of the skull. This through hole 220 thus forms a bone fixture interface section that is contoured to the exposed section of the bone fixture 218. In an exemplary embodiment, the sections are sized and dimensioned such that at least a slip fit or an interference fit exists with respect to the sections. Plate screw 222 is used to secure implantable plate assembly 214 to bone fixture 218. As can be seen in FIG. 2, the head of the plate screw 222 is larger than the hole through the implantable plate assembly 214, and thus the plate screw 222 positively retains the implantable plate assembly 214 to the bone fixture 218. In certain embodiments, a silicon layer 224 is located between the implantable plate 216 and bone 136 of the skull.

Notably, the external portion of a bone conduction auditory prosthesis can be utilized in both the percutaneous application of FIGS. 1A and 1B, and the transcutaneous application of FIG. 2. For example, a bone conduction auditory prosthesis can include a housing containing, e.g., the various modules and elements depicted in FIG. 1B. Those elements include vibration element 160 (FIG. 1B), which is equivalent to vibration element 208 (FIG. 2). The vibration element can be connected to a coupling apparatus 140 (FIG. 1B) or 211 (FIG. 2). Such a coupling apparatus can be connected to an anchor system 162 (FIG. 1B) in a percutaneous bone conduction application. Alternatively, the coupling apparatus can be connected to a plate or other transmission element 212 (FIG. 2) to be utilized in a transcutaneous application. This increases manufacturing efficiencies by allowing the same bone conduction device to be used in either configuration.

Figure 3A:
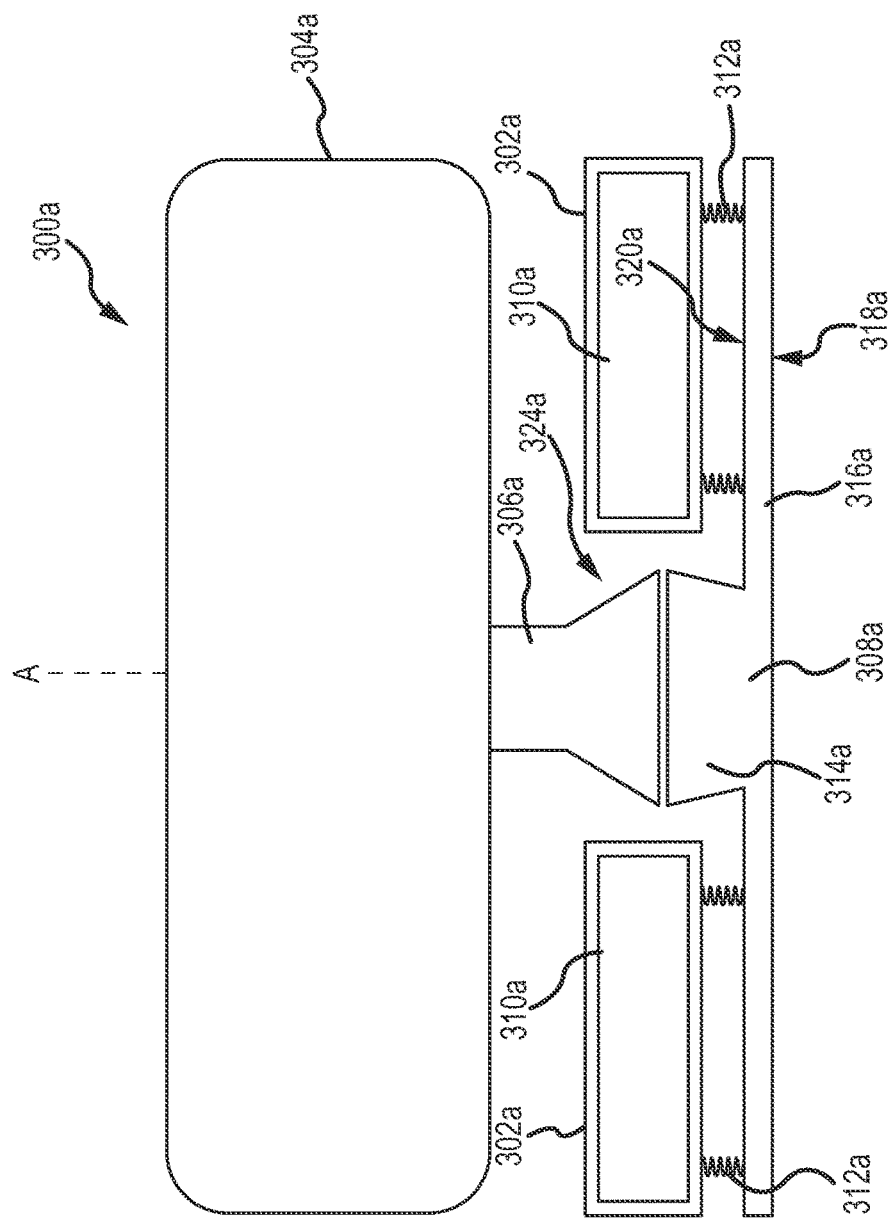
Figure 3C:
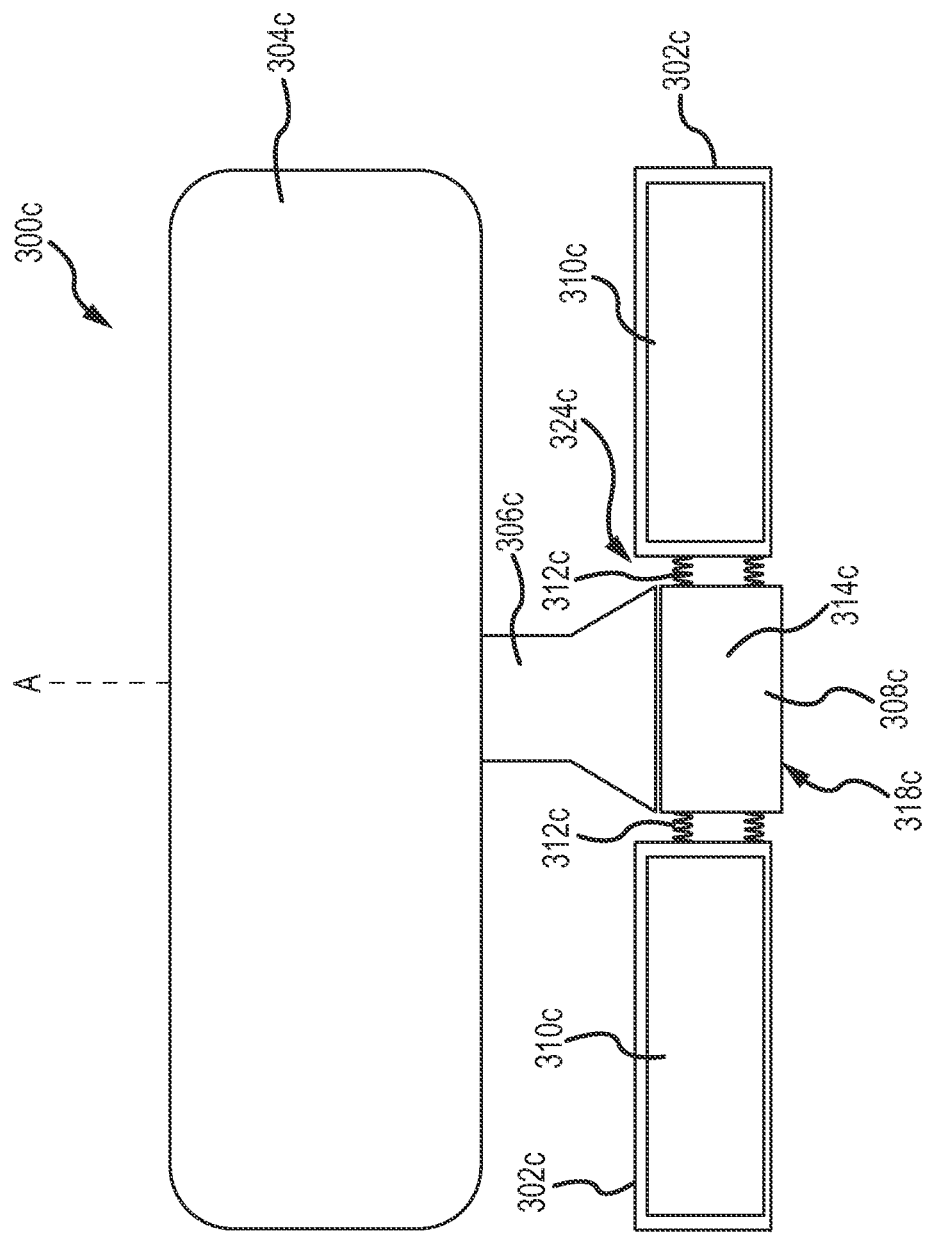

FIGS. 3A-3C depict partial cross-sectional schematic views of external portions 300a-c of transcutaneous bone conduction devices. These depicted embodiments are described generally together followed by a description of each specific embodiment. Each of the depicted embodiments includes a housing 304a-c that includes a vibration element, sound processing electronics, batteries, and other elements disposed therein. These elements are not depicted in the FIGS. A coupling apparatus 306a-c extending from the housing 304a-c is connected to the vibration element. The coupling apparatus 306a-c can be connected to a bone anchor system (in the case of a percutaneous bone conduction device) or to a transmission element 308a-c (in the case of a transcutaneous bone conduction device). An underside 318a-c of the transmission element 308a-c is adapted to contact the skin of a recipient. A magnet housing 302a-c contains one or more masses 310a-c. Either or both of the housing 302a-c and the masses 310a-c are connected to the transmission element 308a-c with one or more resilient elements 312a-c. Different types of resilient elements 312a-c, such as coil springs, leaf springs, torsion springs, shape-memory elements, wave springs, and elastomeric elements, can be utilized in the external portions described herein.

The masses 310a-c can be any type of material that can be utilized to help secure the external portion 300a-c to the skin of a patient, proximate an implanted portion of a bone conduction device. As described above, the external portion 300a-c is held against the skin of a recipient due to magnetic force between elements of the external portion 300a-c and the implanted portion. Thus, the masses 310a-c can be a magnetic component, such as a permanent magnet, a soft magnetic material, or other materials capable of transmitting magnetic flux, e.g., iron, nickel, cobalt, and compositions thereof. In general, utilizing permanent magnets on both an external portion 300a-c and an implanted portion can exhibit the strongest retention forces. However, in other embodiments, the masses 310a-c can be permanent magnets while a soft magnetic material can be utilized in the implanted portion. In yet another embodiment, the masses 310a-c can be a soft magnetic material and permanent magnets can be disposed in the implanted portion. Regardless of the type of magnetic component used, the presence of the masses 310a-c can display undesirable effects on the auditory performance of the auditory prosthesis. In one example, the added weight of the masses 310a-c can reduce the level of force transmitted through the skin by the transmission element 308a-c at higher frequencies. Indeed, the heavier the masses 310a-c, the greater the force reduction. In another example, the masses 310a-c cause increased feedback. This feedback can be at least partially be caused by the pumping of air by the masses 310a-c. To remedy this and other problems, resilient elements 312a-c flexibly connect the housing 302a-c and/or the masses 310a-c to the transmission element 308a-c. By utilizing resilient elements 312a-c, vibration of the masses 310a-c is reduced or eliminated while the transmission element delivers vibrational stimulus to the skull of a recipient. In other embodiments, the masses 310a-c can be incorporated into the vibration element 304a-c. The external portions 300a-c are utilized in conjunction with transcutaneous bone conduction devices and are individually described in more detail below.

Referring to the external portion 300a of FIG. 3A, specifically, the transmission element 308a includes a rigid connection element 314a that connects to the coupling apparatus 306a. The rigid connection element 314a passes through an opening 324a in the magnet housing 302a, which has a substantially annular shape. The connection can be made with a screw, bolt, press-fit connection, threaded connection, adhesive, and/or other mechanical or chemical connections. In certain embodiments, the coupling apparatus 306a can be eliminated such that the rigid connection element 314a can be directly connected to the vibration element 304a. The rigid connection element 314a is connected to, or integral with, a plate 316a that has an external surface 318a that is adapted to contact a skin surface of a recipient when worn. In embodiments, the masses 310a are disposed within a magnet housing 302a and are proximate an internal surface 320a of the plate. One or more resilient elements 312a connect the plate 316a to the magnet housing 302a. An odd or even number of resilient elements 312a can be disposed so as to evenly balance the weight of the masses 310a about an axis A defined by the rigid connection element 314a.

FIG. 3B depicts an external portion 300b having a generally similar configuration to that depicted in FIG. 3A, thus, many of the components are not described further. In this embodiment, the magnet housing 302b and the masses 310b contained therein are disposed proximate an internal surface 320b of a plate 316b. In this case, however, the magnet housing 302b is flexibly connected to the rigid connection element 314b of the transmission plate 316b with one or more resilient elements 312b. An odd or even number of resilient elements 312b can be disposed so as to evenly balance the weight of the masses 310b about axis A. FIG. 3C depicts another embodiment of an external portion 300c with components generally similar to that depicted in FIG. 3A, thus, many of the components are not described further. In this embodiment, the transmission element 308c is the rigid connection element 314c, which has sufficient surface area so as to deliver a vibration stimulus to the skull of a recipient via the external surface 318c. Here, as in FIG. 3B, the magnet housing 302c is flexibly connected to the rigid connection element 314c with one or more resilient elements 312a. An odd or even number of resilient elements 312c can be disposed so as to evenly balance the weight of the masses 310c about the axis A.

Figure 4:
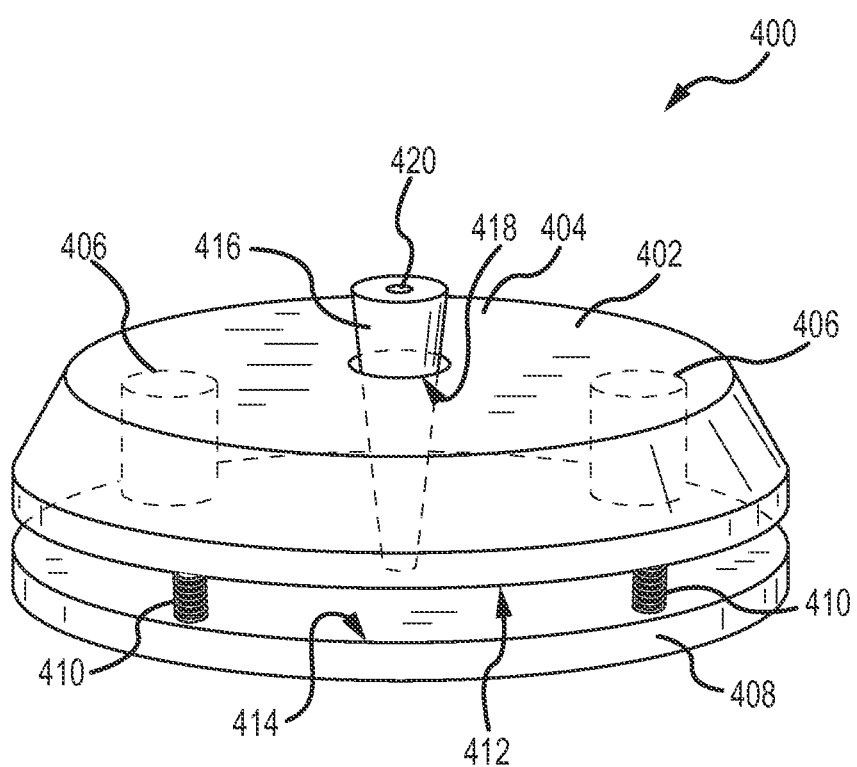
FIG. 4 depicts a partial perspective view of a plate/mass subsystem for use in an external portion of a transcutaneous bone conduction device.

FIG. 4 depicts a partial perspective view of a plate/mass subsystem 400 for use in an external portion of a transcutaneous bone conduction device such as described herein. As described above, an external portion of a bone conduction device can be utilized for both percutaneous and transcutaneous applications. The plate/mass subsystem 400 depicted in FIG. 4 can be connected to the coupling apparatus of the external portion so as to enable the external portion to be utilized in a transcutaneous application. The plate/mass subsystem 400 includes a mass 402 that, in the depicted embodiment, includes a magnet housing 404 having one or more magnets 406 disposed therein. Other materials, such as those described above, can be used in place of the magnets 406. Although two magnets 406 are depicted, other numbers of magnets can be utilized, although it is advantageous to position the magnets about the magnet housing 404 so as to balance the forces attendant therewith.

The mass 402 is connected to a transmission element 408 via a number of resilient members 410, such that a bottom surface 412 of the mass 402 is spaced apart from a top surface 414 of the transmission element 408, which in this embodiment is a plate. A rigid connection element 416 such as a shaft is connected to or integral with a central portion of the transmission element 408. The rigid connection element 416 penetrates a central opening or through-hole 418 defined by both a top surface and a bottom surface of the mass 402, so as to not contact the mass 402. Since the mass 402 is connected to the transmission element 408 with resilient members 410, contact between the connection element 408 and the mass 402 would cause vibrations to be transmitted to the mass 402, thus defeating one of the purposes of the proposed configuration. The rigid connection element 416 includes an interface 420 for releasably securing the rigid connection element 416 to a coupling apparatus of a vibration element, as described above. The interface 420 can be a shaft, a threaded rod, a screw, a bolt, or other connection structure that allows the plate/mass subsystem 400 to be connected to the vibration element of an external portion of an auditory prosthesis. Once secured, the complete external portion can be placed on the head and used as a transcutaneous bone conduction auditory prosthesis. The magnets 406 magnetically couple with one or more implanted magnets proximate the skull of a recipient.

FIG. 5 depicts a partial cross-sectional schematic view of another embodiment of an external portion 500 of a transcutaneous bone conduction device. The external portion 500 includes a housing 502 in which is disposed a vibration element 504. The vibration element 504 is connected directly to a transmission element 508 without, e.g., a coupling apparatus such as described above. Thus, the external portion 500 of FIG. 5 is utilized in a dedicated transcutaneous bone conduction application, unlike certain of the previous embodiments that can be interchanged between transcutaneous and percutaneous applications. In the depicted embodiment, the transmission element 508 includes a shaft 514 connected to or integral with a plate 516. As in the previous embodiments, the plate 516 has a lower surface 518 adapted to contact the skin of a recipient, as well as an upper surface 520. Resilient members 512 flexibly connect the upper surface 520 to one or more masses 510. The external portion 500 also includes a number of additional components 524 required for the functionality of the external portion 500. These are described generally above and can include a battery, electronics, wireless communication devices, sound input elements such as microphones, and so on. To further reduce feedback, the components 524 can be connected to the masses 510 at interface 526. In such an embodiment, the housing 502 can be connected to the transmission element 508 such that vibrations generated by the vibration element 504 are dissipated into the housing 502, while the components 524 are isolated from vibration via the resilient elements 512. In another embodiment, the components 524 can be connected to the housing 502 at interface 528. In such an embodiment, the vibration element 504 and/or transmission element 508 can be connected to the housing via a flexible or resilient connection, not shown.

Figure 6A:
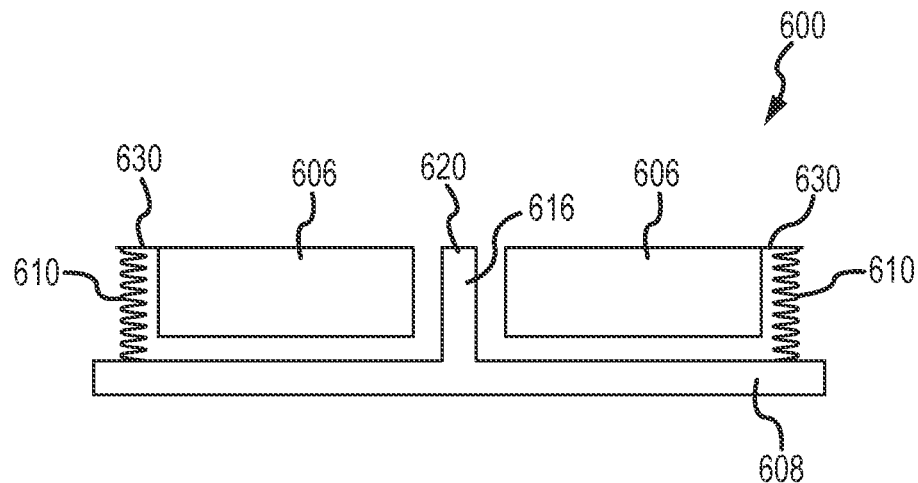
FIGS. 6A and 6B depict partial cross-sectional schematic views of alternative embodiments of plate/mass subsystems for use in an external portion of transcutaneous bone conduction devices.
Figure 6B:
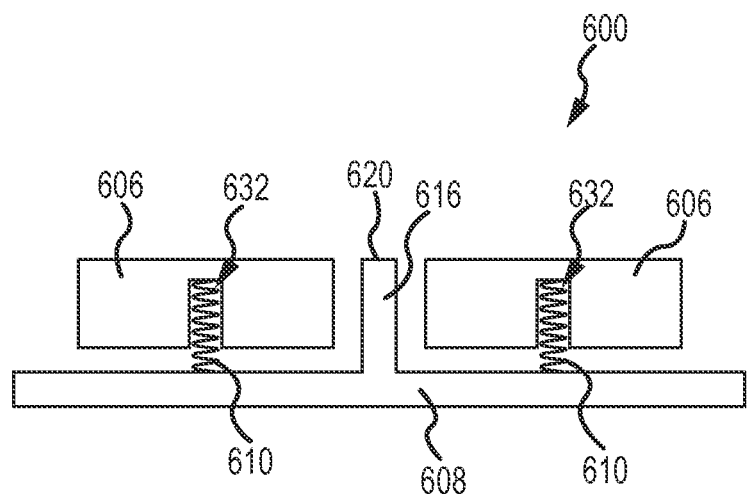

FIGS. 6A and 6B depict partial cross-sectional schematic views of alternative embodiments of plate/mass subsystems 600 for use in an external portion of transcutaneous bone conduction devices. The plate/mass subsystems 600 of both FIGS. 6A and 6B are described together. Each plate/mass subsystem 600 includes a transmission element 608 having a form factor in the shape of a plate, although other configurations are contemplated. A rigid connection element 616 extends from the transmission element 608 and includes an interface 620 can be a shaft, a threaded rod, a screw, a bolt, or other connection structure that allows the plate/mass subsystem 600 to be connected to the vibration element of an external portion of an auditory prosthesis. Masses 606 can be magnetic components such as described above. In FIG. 6A, the masses 606 include one or more arms 630 that can extend from the mass 606. The arm 630 provides a point of connection for a resilient element 610 that connects the mass 606 to the transmission element 608. Similarly the masses 606 of FIG. 6B can define bores 632 therein. One or more resilient elements 610 can be disposed in the bores 632 to resiliently connect the masses 606 to the transmission element 608. Contrasted with the embodiments described above where the resilient elements are connected to a lower surface of a mass, the configurations depicted in FIGS. 6A and 6B connect the resilient elements 610 proximate an upper portion of the masses 606. This can also allow for use of smaller masses 606 than might otherwise be utilized in the embodiments where resilient elements are connected to the underside of the mass (for example, as depicted in FIG. 3A).

Figure 7:
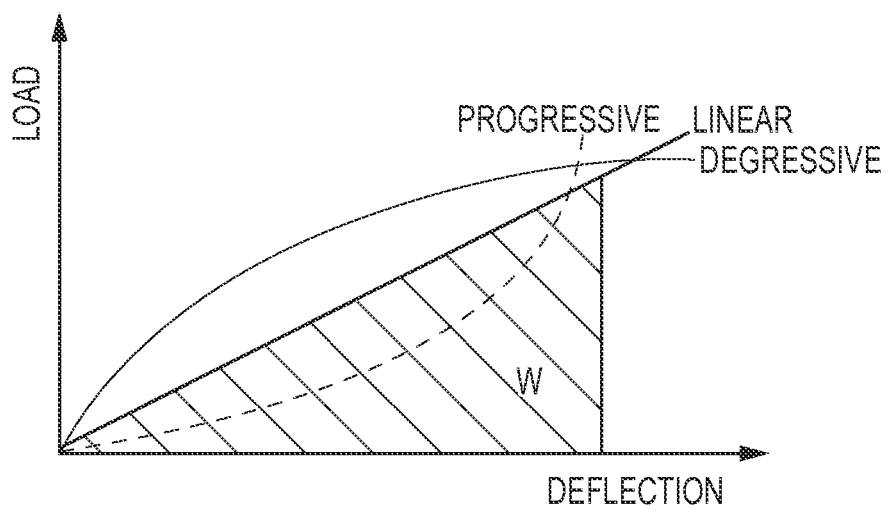
FIG. 7 depicts spring deformation curves for springs utilized in an external portion of a transcutaneous bone conduction device.

FIG. 7 depicts spring deformation curves for springs utilized in an external portion of a transcutaneous bone conduction device. Again, different types of resilient elements, such as coil springs, leaf springs, torsion springs, shape-memory elements, wave springs, and elastomeric elements, can be utilized in the external portions described herein. FIG. 7 depicts curves for springs with linear characteristics, degressive characteristics, and progressive characteristics, each of which can be utilized in conjunction with the embodiments described herein. The label W depicts work performed in the spring. In certain embodiments, a degressive spring can be desirable, as it will minimize the required length of compression from the static magnetic attraction force (e.g., the force generated by attraction to an implanted portion of an auditory prosthesis and an associated magnet). Such a degressive spring is non-linear with respect to force and length and still allows for a low spring constant (e.g., a weak spring) in the working range, which allows for a low decoupling frequency.

This disclosure described some embodiments of the present technology with reference to the accompanying drawings, in which only some of the possible embodiments were shown. Other aspects, however, can be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments were described herein, the scope of the technology is not limited to those specific embodiments. One skilled in the art will recognize other embodiments or improvements that are within the scope of the present technology. Therefore, the specific structure, acts, or media are disclosed only as illustrative embodiments. The scope of the technology is defined by the following claims and any equivalents therein.

What is claimed is:

1. An auditory prosthesis comprising:
a housing;
a mass disposed in the housing and configured to facilitate securing the auditory prosthesis relative to an implanted component;
a vibration element disposed within the housing;
a transmission element connected to the vibration element and disposed proximate an outer surface of the housing; and
a resilient element coupling the mass to the transmission element,
wherein the mass is separate from the vibration element.

2. The auditory prosthesis of claim 1, wherein the mass comprises a magnet housing and a magnet secured within the magnet housing, and wherein the resilient element is connected to the magnet housing.

3. The auditory prosthesis of claim 1, wherein the mass comprises at least one magnetic component.

4. The auditory prosthesis of claim 1, wherein the resilient element comprises a plurality of resilient elements.

5. The auditory prosthesis of claim 1, wherein the resilient element comprises at least one of a coil spring, a leaf spring, a torsion spring, a shape-memory element, a wave spring, and an elastomeric element.

6. The auditory prosthesis of claim 1, wherein the mass is adapted to magnetically couple to a magnetic component disposed remote from the housing.

7. The auditory prosthesis of claim 1, further comprising:
a microphone; and
a sound processor coupled to the microphone, wherein the sound processor and the microphone are secured to the transmission element through the mass.

8. The auditory prosthesis of claim 1, wherein the resilient element is non-linear with respect to force and length.

9. The auditory prosthesis of claim 1,
wherein the transmission element comprises:
a bottom exterior surface adapted to contact skin of a recipient of the auditory prosthesis; and
an upper exterior surface opposite the bottom exterior surface; and
wherein the resilient element couples the mass to the transmission element solely via the upper exterior surface of the transmission element.

10. An apparatus comprising:
a transmission element adapted to be releasably secured to a vibration element of an auditory prosthesis;
a mass configured to facilitate securing the auditory prosthesis relative to an implanted portion of the apparatus; and
a resilient element flexibly connecting the transmission element to the mass,
wherein the mass is separate from the vibration element; and
wherein the mass is disposed relative to the transmission element such that the mass is disposed between the transmission element and the auditory prosthesis when the transmission element is releasably secured to the vibration element of the auditory prosthesis.

11. The apparatus of claim 10, wherein the mass comprises one or more arms extending from the mass, wherein the resilient element flexibly connects the transmission element to the mass via the one or more arms.

12. The apparatus of claim 11, wherein the resilient element is non-linear with respect to force and length.

13. The apparatus of claim 10, further comprising:
a shaft,
wherein the transmission element comprises a plate connected at a central location to the shaft; and
wherein the transmission element is adapted to be releasably secured to the vibration element via the shaft.

14. The apparatus of claim 13, wherein the resilient element is flexibly connected to the shaft.

15. The apparatus of claim 10, wherein the mass defines one or more bores, and wherein the resilient element is disposed in at least one of the one or more bores to connect the transmission element to the mass.

16. The apparatus of claim 10, wherein the mass comprises a housing and at least one magnetic component disposed in the housing.

17. The apparatus of claim 16, further comprising a rigid connection element secured to the transmission element and extending through a central opening defined by the housing.

18. The apparatus of claim 10, wherein the resilient element comprises a plurality of resilient elements.

19. The apparatus of claim 18, wherein the plurality of resilient elements comprises at least one of a coil spring, a leaf spring, a torsion spring, a shape-memory element, a wave spring, and an elastomeric element.

20. An apparatus comprising:
a housing comprising a top exterior surface and a bottom exterior surface and defining a through-hole from the top exterior surface to the bottom exterior surface;
at least one mass disposed in the housing for securing the apparatus relative to an implanted component;
a resilient member connected to at least one of the bottom exterior surface and the at least one mass; and
a transmission element connected to the resilient member such that the transmission element is suspended below the bottom exterior surface by the resilient member,
wherein the resilient member is configured to resist vibration of the at least one mass from vibrational stimulus delivered by the transmission element.

21. The apparatus of claim 20, further comprising a rigid connection element secured to and extending from the transmission element through the through-hole.

22. The apparatus of claim 21, wherein the rigid connection element does not contact the through-hole.

23. The apparatus of claim 21, wherein the rigid connection element comprises at least one of a shaft, a threaded rod, a screw, and a bolt.

24. The apparatus of claim 20, wherein the resilient member comprises a plurality of resilient members.

25. The apparatus of claim 24, wherein the plurality of resilient members comprises at least one of a coil spring, a leaf spring, a torsion spring, a shape-memory element, a wave spring, and an elastomeric element.

26. The apparatus of claim 20, wherein the resilient member is non-linear with respect to force and length.

* * * * *